US010426541B2

(12) United States Patent
Haiat et al.

(10) Patent No.: US 10,426,541 B2
(45) Date of Patent: Oct. 1, 2019

(54) DEVICE FOR ASSISTING WITH THE PLACEMENT OF AN ORTHOPEDIC INSTRUMENT

(71) Applicant: CENTRE NATIONAL DE LA RECHERCHE SCIENTIFIQUE (CNRS), Paris (FR)

(72) Inventors: Guillaume Haiat, Saint Maurice (FR); Vincent Mathieu, Paris (FR); Adrien Michel, Arcueil (FR)

(73) Assignee: CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 567 days.

(21) Appl. No.: 14/677,050

(22) Filed: Apr. 2, 2015

(65) Prior Publication Data

US 2015/0282856 A1 Oct. 8, 2015

Related U.S. Application Data

(60) Provisional application No. 61/974,072, filed on Apr. 2, 2014.

(51) Int. Cl.
*A61F 2/46* (2006.01)
*A61B 17/92* (2006.01)
*A61B 90/00* (2016.01)

(52) U.S. Cl.
CPC .............. *A61B 17/92* (2013.01); *A61B 90/06* (2016.02); *A61F 2/4609* (2013.01);
(Continued)

(58) Field of Classification Search
CPC .................. A61F 2/4609; A61F 2/4657; A61F 2002/4666; G01L 5/0052; G01L 19/0609;
(Continued)

(56) References Cited

U.S. PATENT DOCUMENTS

| 5,079,728 | A  | * | 1/1992  | Adams      | G01N 3/48 702/42        |
|-----------|----|---|---------|------------|-------------------------|
| 5,209,483 | A  | * | 5/1993  | Gedney     | A63B 69/0026 473/223    |
| 6,224,605 | B1 | * | 5/2001  | Anderson   | A61B 17/15 606/85       |
| 6,748,791 | B1 | * | 6/2004  | Georgeson  | G01M 7/08 73/12.01      |
| 6,827,695 | B2 | * | 12/2004 | Palazzolo  | A61B 5/04012 601/41     |
| 7,900,498 | B1 | * | 3/2011  | Ratcliffe  | G01L 5/0052 73/12.01    |

(Continued)

FOREIGN PATENT DOCUMENTS

EP 1 433 445 6/2004

*Primary Examiner* — Zade Coley
*Assistant Examiner* — Amy R Sipp
(74) *Attorney, Agent, or Firm* — Osha Liang LLP (57) ABSTRACT

A device (1) assisting with the placement of an orthopedic instrument (2) intended to be inserted in a receiving bone (3) by impaction, by means of an impacter (10) comprising at least one striking surface (11) designed to come into contact with an impact surface coupled to said orthopedic instrument in order to apply an impaction force to said orthopedic instrument (2), said device being characterized in that it comprises a force sensor (12) able to measure, upon each impact, said impaction force applied by the impacter (10) to said impact surface and to supply a measurement signal indicative of the temporal variation of said applied impaction force, said force sensor (12) being connected to processing means (30) designed to determine, on the basis of the temporal variation of said impaction force supplied for each impact in succession, an indicator representative of the degree of insertion of said orthopedic instrument (2) in the receiving bone (3).

16 Claims, 2 Drawing Sheets

(52) U.S. Cl.
CPC ...... *A61F 2/4657* (2013.01); *A61B 2090/064* (2016.02); *A61F 2002/4666* (2013.01); *A61F 2002/4681* (2013.01)

(58) Field of Classification Search
CPC ............... G01N 29/045; G01N 1/2208; G01N 2015/0261; G01N 3/48; B25D 2250/195; B25D 2250/201; B25D 2250/221; B25D 11/04; B25D 11/125; B25D 16/00; B25D 2211/068; B25D 2216/0015; B25D 2216/0023; B25D 2250/021; B25D 2250/095; A61B 17/1659; A61B 17/92; A61B 2017/922
USPC ............. 606/85, 91, 99, 100, 102; 73/12.01, 73/12.08, 12.09, 81; 173/117
See application file for complete search history.

(56) References Cited

U.S. PATENT DOCUMENTS

| | | | |
|---|---|---|---|
| 2004/0200263 A1* | 10/2004 | Saegusa | A63B 53/04 73/11.01 |
| 2008/0125671 A1* | 5/2008 | Meneghini | A61B 90/06 600/553 |
| 2010/0005571 A1* | 1/2010 | Moss | A42B 3/046 2/410 |
| 2010/0249796 A1* | 9/2010 | Nycz | A61F 2/4609 606/99 |
| 2011/0259076 A1* | 10/2011 | Faulkner | A61B 5/11 73/1.01 |

* cited by examiner

DEVICE FOR ASSISTING WITH THE PLACEMENT OF AN ORTHOPEDIC INSTRUMENT

TECHNICAL FIELD OF THE INVENTION

The invention relates to a device assisting with the placement of an orthopedic instrument intended to be inserted in a receiving bone by impaction, by means of a percussion tool, or impacter, able to apply an impaction force to said orthopedic instrument.

BACKGROUND OF THE INVENTION

The term orthopedic instrument denotes all implants for orthopedic prostheses intended to be implanted in bony tissue in order to carry out replacement of deficient joints, and also ancillary devices used to prepare the receiving bone in order to allow the placement of the definitive implant and, in particular, the surgical rasps used for orthopedic implants. Within the category of orthopedic prostheses, the number of implants available are many. Total hip prostheses, knee prostheses, shoulder prostheses or even elbow, ankle or spine prostheses are notable examples.

One field of application of the present invention is chiefly, although not exclusively, the placement of orthopedic instruments for hip prostheses. The vast majority of the proposed types of hip prosthesis have in common a first part, consisting of a femoral stem intended to be implanted in the medullary cavity of the femur and a prosthetic head formed of a spherical component, possibly removable, which takes the place of the head of the femur, and a second part, consisting of a prosthetic acetabulum, intended to be implanted in the acetabular cavity situated at the lateral face of the iliac bone. The prosthetic acetabulum, which is therefore intended to replace the joint part of the pelvis, is more specifically made up of an acetabular cup, which is an approximately hemispherical component, generally made of metal, implanted in the pelvic bone and into which an insert with which the prosthetic head is articulated is placed.

In particular, the placement of the prosthetic acetabulum in the bony cavity may be performed by simple impaction, using a placement ancillary provided for that purpose, by means of which the prosthetic acetabulum is impacted by the surgeon, using an impacter, typically a hammer, that strikes the placement ancillary. One example of an ancillary for the placement of the prosthetic acetabulum consists of a rigid manipulation handle provided in its distal part with a holding head, that allows the acetabulum to be held and then positioned up to the site of impaction of the acetabulum into the bony cavity of the hip and, in its proximal part, with an impact surface intended to be impacted by means of a striking face of the impacter provided for this purpose so as to apply the impaction force necessary for the placement of the prosthetic acetabulum in the bony cavity.

Surgical success in the placement of the prosthetic acetabulum and, more generally, of an orthopedic prosthesis implant intended to be implanted by impaction, relies on this implant achieving a sufficient degree of insertion into the receiving bone, on which the biomechanical stability will be dependent. This biomechanical stability is in actual fact determined by two distinct phenomena:

the primary stability, which corresponds to the degree of attachment or anchorage of the prosthetic element in the bone immediately after the operation (immediate postoperative stability), and which is dependent on the quality of the bone and of the surgical procedure, which will be detailed later on;

the secondary stability, which corresponds to the bone regrowth through osteointegration phenomena and which is dependent on the primary stability and on the ability of the bone to heal.

According to the conventional surgical procedure, the surgeon bores into the bone of the pelvis to create a hemispherical cavity that can retain the implant, while at the same time stimulating bone regrowth phenomena which will make it possible to improve osteointegration during the healing phase. Once the cavity has been produced, the surgeon inserts the prosthetic acetabulum forcefully into the cavity by impaction using the impacter and the placement ancillary until he considers that the implant has reached a sufficient degree of insertion that good primary stability of the implant is achieved, but without causing the bone to fracture. The primary stability is indeed an essential element in the success of the surgery. Typically, good primary stability corresponds to a placement situation in which the degree of insertion of the implant is optimal, this being manifested in a maximum area of contact between the bone and the implant. However, it is difficult these days for the surgeon to be able to quantify in fine detail the number and force of the impacts that need to be generated on the placement ancillary using the impacter in order to obtain good primary stability without thereby damaging the receiving bone. Therefore a compromise needs to be reached between impact energy that is high enough to obtain good primary stability, which corresponds to a maximum area of contact between the bone and the implant, and impact energy low enough not to risk preoperative fracturing of the receiving bone.

Now, these days, only empirical methods are used. Typically, during the operation, the surgeons rely on their own experience and, in particular, on the noise of the impact in order to determine whether they need to hit harder or less hard and/or whether they need to continue to apply hammer blows. However, by using this type of method, the surgeons are not able to have absolute certainty that the degree of insertion of the implant into the receiving bone is optimal. Furthermore, one of the disadvantages inherent to the application of this method is that when the implant is insufficiently inserted into the bone, the latter may then become detached from its support. That may result in significant lesions in the cavity bored into the receiving bone. When that happens, the surgeon will therefore have for example to operate again in order to enlarge the bony cavity, something which will then allow a new implant of suitable dimensions to be positioned.

Patent document EP1433445 discloses a method for preoperatively measuring the mechanical stability of an orthopedic prosthesis which is intended to be implanted in a bone by forced insertion, which method is intended to assist the surgeon in estimating the stability of the implant. This method consists in measuring a relative slippage of the prosthesis with respect to the receiving bone under the action of a suitably predetermined test load applied to the prosthesis or to the receiving bone. However, this method relies on a complex procedure.

Moreover, this identified need to be able to evaluate in fine detail the number of impacts required in order to achieve a sufficient degree of insertion without the risk of causing preoperative fractures of the receiving bone is also encountered when implementing the surgical procedure that involves impacting an orthopedic implant surgical rasp, particularly a femoral rasp for a hip prosthesis. What happens is that this type of rasp is conventionally used in order to make a hole in the medullary cavity of the femur by "milling" the bone so as, on the one hand, to prepare the shape of the cavity so that the implant is a perfect fit therein and, on the other hand, to stimulate bone regrowth by removing superficial bony tissue. These orthopedic rasps are not an element of the implant (such as the acetabulum or the femoral stem) because they are removed after they have been impacted, so as to allow the definitive implant to be placed. However, the placement principle is similar insofar as it involves directly impacting the rasp with the impacter (without the intermediary of an ancillary), until a sufficient degree of insertion is achieved, taking care not to cause the receiving bone in which the rasp is inserted to fracture.

SUMMARY OF THE INVENTION

In this context, one object of the present invention is to propose a device for assisting with the placement of an orthopedic instrument in a receiving bone which makes it possible to provide a precise evaluation of the degree of insertion of the orthopedic instrument in the receiving bone during the operation, offering the surgeon a veritable tool that assists with decision-making capable of informing him in real time notably as to the primary stability of orthopedic implants while at the same time being simple to use and to implement.

To this end, the invention relates to a device assisting with the placement of an orthopedic instrument intended to be inserted in a receiving bone by impaction, said device comprising an impacter comprising at least one striking surface designed to impact an impact surface coupled to said orthopedic instrument in order to apply an impaction force to said orthopedic instrument. According to the invention, the device comprises a force sensor able to measure, upon each impact, said impaction force applied by the impacter to said impact surface and to supply a measurement signal indicative of the temporal variation of said applied impaction force, said force sensor being connected to processing means designed to determine, on the basis of the temporal variation of said impaction force supplied for each impact in succession, an indicator representative of the degree of insertion of said orthopedic instrument in the receiving bone.

The invention therefore relies on the implementation of a simple force sensor which delivers measurement signals able to interpret the temporal variation in the force applied for each impact in succession, the logging and analysis of which will make it possible to determine an indicator that reveals the firmness of the contact between bone and orthopedic instrument and thereby the degree of insertion of the orthopedic instrument in the receiving bone. The device of the invention therefore allows the surgeon to be informed, in real time, as to the degree of insertion achieved during the intervention of inserting the orthopedic instrument into the receiving bone. What is more, in addition to its low cost, the device of the invention is particularly simple to use and advantageously does not in any way alter the way in which the surgeon performs the operation.

Advantageously, said indicator is determined by said processing means as being the mean of said applied impaction force, calculated over a time interval of programmable duration positioned on said measurement signal, the instant marking the start of said time interval being defined with respect to an instant corresponding to the maximum amplitude of said measurement signal.

It has been possible to demonstrate that the indicator thus constructed is correlated with the pull-out force, namely with the force that has to be applied in order to pull the orthopedic instrument out of its anchorage in the receiving bone. Put differently, the indicator thus constructed provides an evaluation of the pull-out force, which is a determining factor in implant stability.

According to a first embodiment, the instant marking the start of said time interval coincides with the instant corresponding to the maximum amplitude of said measurement signal.

For preference, according to this first embodiment, said time interval has a duration of between 1.2 ms and 2 ms, advantageously between 1.4 ms and 1.8 ms, and more advantageously still, equal to 1.6 ms.

According to a second embodiment, the instant marking the start of said time interval is defined with a predetermined delay with respect to the instant corresponding to the maximum amplitude of said measurement signal.

For preference, according to this second embodiment, said time interval has a predefined duration of less than 10 ms.

For preference said indicator is calculated as follows:

$$I_1 = \frac{1}{A_1 \cdot (t_2 - t_1)} \int_{t_1}^{t_2} A(t) \cdot dt$$

where:

$A(t)$ corresponds to the amplitude of said measurement signal at the instant t;

$A_1$ corresponds to the maximum amplitude of said measurement signal; and $t_1$ and $t_2$ correspond respectively to the instants marking the start and the end of said time interval.

As an alternative, said indicator is determined by said processing means as being the impact duration measured from said temporal variation.

Advantageously, said processing means comprise means of testing the convergence of said indicator toward a steady value of said indicator as a function of the number of impacts, so as to evaluate said degree of insertion of said orthopedic instrument into the receiving bone.

According to one embodiment, said processing means of the invention are designed to detect when said indicator reaches a saturation level, indicating that said degree of insertion is sufficient. Specifically, if the indicator reaches a substantially stable level beyond a certain number of impacts, this means that the firmness of the contact between the orthopedic instrument and the receiving bone is no longer varying, which means that the degree of insertion is considered to be optimal or, in any case, to be sufficient.

As an alternative, the processing means may also compare the value of the indicator with a threshold value defined using charts.

Advantageously, said processing means are coupled to audible and/or visible warning means able to provide a visible and/or audible indication when the degree of insertion of said orthopedic instrument in the receiving bone as evaluated by said processing means is sufficient.

Said orthopedic instrument may consist of an implant for an orthopedic prosthesis, said impacter acting to impact said implant in collaboration with a placement ancillary consisting of a rigid manipulations handle provided in its distal part with a head for holding said implant and, in its proximal part, with said impact surface.

Said orthopedic instrument may also consist of an orthopedic implant surgical rasp, notably a femoral rasp for a hip prosthesis, comprising a part for holding which at its upper end is provided with said impact surface.

In one embodiment, said force sensor may be mounted on said striking surface of said impacter.

In another embodiment, said force sensor may be mounted on said impact surface.

According to one embodiment, said force sensor may consist of strain gauges.

As an alternative, said force sensor may consist of an accelerometer.

The invention also relates to a method for processing a signal representative of an impaction force applied by means of a striking surface of an impacter to an impact surface coupled to an orthopedic instrument intended to be inserted in a receiving bone by impaction, said method comprising steps in which:

a force sensor with which said striking surface of said impacter is equipped is used to gather a measurement signal indicative of the temporal variation of said impaction force applied by the impacter to said impact surface upon each impact, the temporal variation of said impaction force supplied for each impact in succession is used to determine an indicator representative of a degree of insertion of said orthopedic instrument in the receiving bone.

The method advantageously comprises a step of testing the evolution of said indicator as a function of the number of impacts, in which step the convergence of said indicator toward a steady value of said indicator as a function of the number of impacts is monitored so as to evaluate said degree of insertion of said orthopedic instrument in the receiving bone.

The method preferably comprises a step of operating audible and/or visual alarm means when said indicator reaches said steady value or a threshold value defined beforehand using charts.

The method described hereinabove can be implemented by digital processing means, for example a microprocessor, a microcontroller or the like.

BRIEF DESCRIPTION OF THE DRAWINGS

Other features and advantages of the invention will become clearly apparent from the description thereof given hereinafter of one particular embodiment of the invention given by way of entirely nonlimiting indication, with reference to the attached drawings in which.

DESCRIPTION OF EMBODIMENTS

Figure 1:
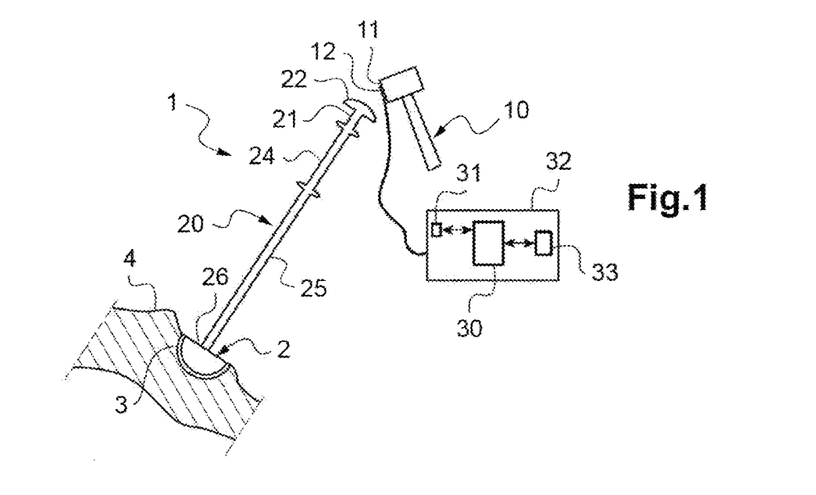
FIG. 1 is a schematic depiction of a device for assisting with the placement of an orthopedic prosthesis implant according to the invention.

FIG. 1 depicts a device 1 for assisting with the placement of an orthopedic instrument 2, which in this example consists of an implant for an orthopedic prosthesis and in particular of a prosthetic acetabulum 2 which is intended to be inserted progressively by impaction into a receiving bone 3 formed by a bony cavity in the hip 4 of the patient. The device 1 comprises a percussion tool or impacter 10, of the hammer or equivalent type, used by the surgeon to produce an impact on the prosthetic acetabulum 2 via an ancillary 20 used for the placement of the prosthetic acetabulum 2. The placement ancillary 20 essentially comprises a handle comprising a rigid rod 21 to the proximal end of which is rigidly fixed a knob having a substantially convex surface 22 forming an impact surface. Working from the proximal end of the rod 21 toward the distal end thereof, the rod 21 also comprises a manipulation handgrip 24 secured to the rod 21, then a portion 25 ending in a head 26 for holding the prosthetic acetabulum 2, which head is not illustrated in detail.

The impacter 10 itself comprises a striking surface 11 intended to impact the impact surface 22 of the placement ancillary 20, in order to apply the impaction force needed to place the implant 2 in the bony cavity 3. A number of impacts of substantially the same intensity are preferably performed by means of the impacter in order to drive the orthopedic instrument, in this particular instance the prosthetic acetabulum, progressively into the receiving bone. Furthermore, the direction of the impaction force is substantially aligned on the axis of the implant.

As explained above, the invention also applies to the placement of an orthopedic instrument of orthopedic implant surgical rasp type, notably a femoral rasp for a hip prosthesis. In this case, the rasp is designed to be impacted directly by the impacter 10, preferably with substantially the same intensity, without the intermediary of a placement ancillary, and the corresponding impact surface is then formed by a surface provided for that purpose, arranged at an upper end of a part of the rasp that is for holding.

According to the exemplary embodiment of FIG. 1, the impacter 10 is equipped with a force sensor 12 able to be positioned on the striking surface 11 that is intended to come into contact with the impact surface 22 of the placement ancillary 20. This force sensor 12 is intended to convert into a usable electrical signal the impaction force applied to the impact surface 22 of the placement ancillary upon each strike with the impacter 10 for inserting the implant 2 into the bony cavity 3. According to one exemplary embodiment, the force sensor may consist of strain gauges or deformation gauges arranged at the striking surface 11 of the percussion tool 10 and connected in a suitable layout. As an alternative, the force sensor may consist of an accelerometer.

According to another embodiment (not depicted), the force sensor 12 may be positioned on the impact surface 22 of the placement ancillary 20 (or of the orthopedic instrument itself, in the case where it is an orthopedic rasp that is being placed by impaction).

Moreover, the device of the invention comprises processing means 30, coupled to the force sensor 12 and designed, as will be explained in greater detail later, to evaluate the degree of insertion of the implant 2 in the receiving bone 3 from measurement signals delivered by the force sensor 12. These processing means 30, such as a microprocessor, are associated with a memory 31 intended to record the measurement signals provided by the force sensor 12, the processing means 30 and the memory 31 for example being assembled onto a printed circuit. The processing means 30 are, for example, housed in an external housing 32. As an alternative, the processing means 30 may also be incorporated into the device which is equipped with the force sensor (the impacter, the placement ancillary or an orthopedic instrument in the case of a rasp, depending on the various embodiments). For preference, the connection between the force sensor 12 and the processing means 30 is a wired connection using a lead. In another alternative form, measurement signals acquired by the force sensor 12 could also be transmitted using a wireless connection.

With reference to FIG. 1, upon each strike with substantially the same intensity performed using the impacter 10 on the placement ancillary 20, the force sensor 12 is designed to record the impaction force applied dynamically. More specifically, upon each successive strike required for the placement of the prosthetic acetabulum, the force sensor 12 is able to supply a measurement signal indicative of the temporal variation in said applied impaction force. Thus, as illustrated in FIG. 2, the processing means 30 have available, for each impact, a signal pertaining to the temporal variation in the applied impaction force.

Figure 2:
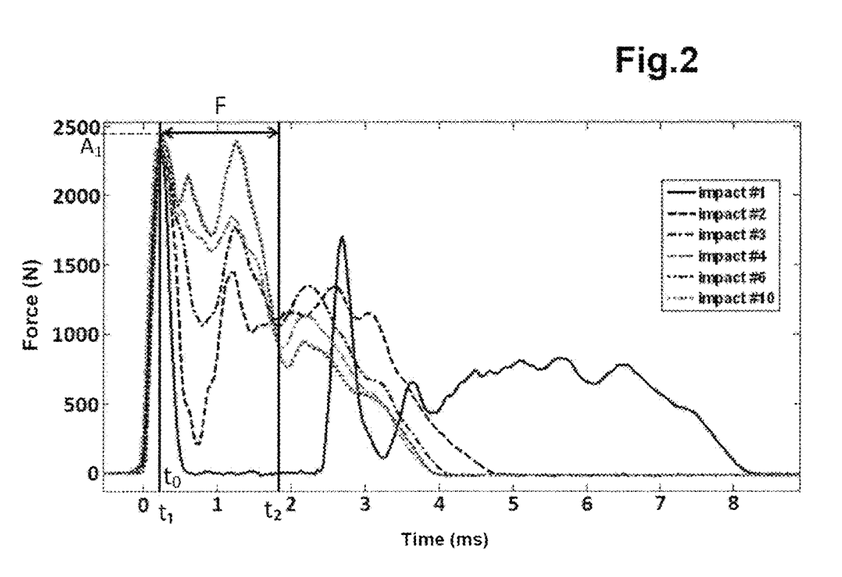
FIG. 2 is a diagram illustrating one example of six measurement signals corresponding to the variation in the force applied to the placement ancillary as a function of time during the various impacts and illustrating the calculation of an indicator representative of the degree of insertion of the implant in the receiving bone corresponding to the mean of the signal calculated over a predefined integration time interval.

FIG. 2 by way of example shows six such measurement signals, corresponding to the temporal variation in the impaction force applied, during various impacts, these respectively being the first, the second, the third, the fourth, the sixth and the tenth impact performed during a test insertion of the prosthetic acetabulum into a receiving bone. This test was conducted using by way of impacter the same 3.5 kg mass released onto the impact surface of the placement ancillary from a height of 4 cm so as to reproduce impacts of roughly the same intensity during the duration of the insertion test. As FIG. 2 shows, the profile of the temporal variation in impaction force applied by the impacter to the placement ancillary varies greatly according to the rank of the impact. Now, it has been possible to demonstrate that this temporal variation in the impaction force applied during an impact with substantially the same intensity is directly dependent on the firmness of the contact between the implant and the receiving bone and on the pull-out force.

So, the invention is based on the measurement of the temporal variation in impaction force between the impact surface of the placement ancillary and the striking surface of the impacter in order to determine an indicator capable of qualifying this state of firmness of the contact between the implant and the receiving bone and, thereby, the degree of insertion of the implant into the receiving bone and the pull-out force. Specifically, the increase in the degree of insertion of the implant into the receiving bone is connected with the increase in the area of contact between the implant and the receiving bone, which leads to an increase in the firmness of the contact between the implant and the bone, which may advantageously be revealed by analyzing the temporal variation of the impaction force between the placement ancillary and the impacter.

A first alternative form that allows such an indicator to be constructed using the processing means of the invention involves determining the mean of the impaction force applied, during each impact, and calculated over a time interval of programmable duration positioned on the measurement signal supplied by the sensor, the start of this time interval preferably being defined with respect to an instant corresponding to the maximum amplitude of the measurement signal. In other words, the time interval allows the measurement signal corresponding to the temporal variation in impaction force to be integrated over a programmable period of time.

According to a first embodiment, with reference to FIG. 2, during the processing of the measurement signal resulting from each impact, the instant $t_1$ marking the start of the integration time interval F, or lower limit of integration, is defined in such a way that it corresponds with the instant $t_0$ corresponding to the maximum amplitude $A_1$ of the measurement signal. Indeed, the shape and amplitude of the spike corresponding to the maximum amplitude is characteristic for each measurement signal acquired, which makes it an easily reproducible common point of reference for the integration bottom limit of the signal. According to this embodiment, the integration time interval therefore begins at the instant corresponding to the maximum amplitude $A_1$ of the measurement signal. According to this first embodiment, the instant $t_2$ marking the end of the time interval F for the integration of the measurement signal, or integration top limit, is chosen so that the integration time interval F has a duration of between 1.2 ms and 2 ms, advantageously between 1.4 ms and 1.8 ms, and preferably equal to 1.6 ms.

Figure 3:
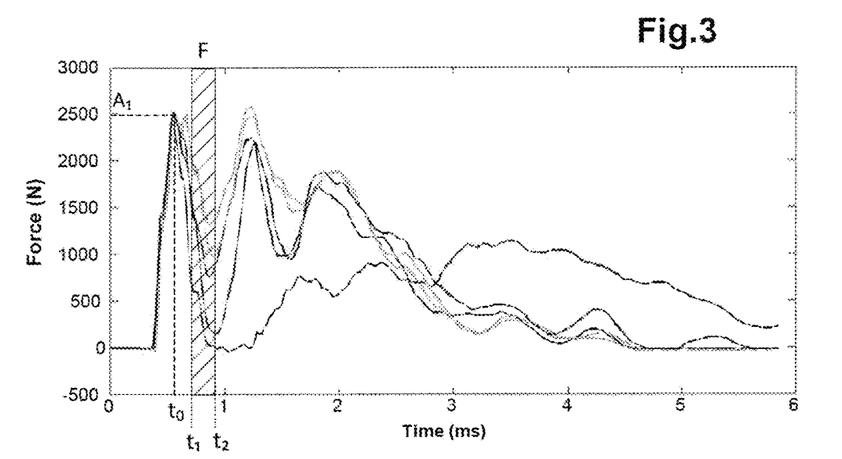
FIG. 3 is a diagram illustrating another embodiment for the positioning of the integration time interval used for calculating the indicator according to the invention.

FIG. 3 illustrates another embodiment for defining the position and duration of the integration time interval allowing the indicator according to the invention to be constructed. FIG. 3 illustrates the results of a series of tests on the insertion of a prosthetic acetabulum into receiving bones of different diameters, respectively 49, 49.5, 50, 50.5 and 51 mm in diameter, always with impacts of substantially the same intensity, and FIG. 3 more specifically illustrates the various signals indicating the temporal variation in the impaction force applied by the impacter to the placement ancillary during the last impact of each series of tests, for the five receiving bones of different diameters, respectively 49, 49.5, 50, 50.5 and 51 mm in diameter.

In particular, according to this other embodiment for the positioning of the integration time interval F, the instant $t_1$ marking the start of the integration time interval F, or in other words the integration bottom limit of the measurement signal, is defined with a predetermined delay with respect to the instant $t_0$ corresponding to the maximum amplitude $A_1$ of the measurement signal. For example, the limits of the integration time interval F are chosen as follows: $t_1=t_0+0.391$ ms and $t_2=t_0+0.527$ ms. It has been possible to observe that calculating the mean of the signal over such an integration time interval was suitable for obtaining a reliable and relevant indicator of the degree of insertion of the implant and therefore of the stability of the latter. However, the duration of the integration time interval F may be modified appreciably, without substantially affecting the results, and may preferably have a predefined duration less than or equal to 10 ms. It may for example be between 0.080 ms and 0.2 ms, more advantageously between 0.098 ms and 1.175 ms. Once the integration time interval F has been positioned according to one or other of the embodiments explained hereinabove, the indicator representative of the degree of insertion of the implant into the receiving bone can be calculated as follows:

$$I_1 = \frac{1}{A_1 \cdot (t_2 - t_1)} \int_{t_1}^{t_2} A(t) \cdot dt$$

where:

A(t) corresponds to the amplitude of said measurement signal at the instant t;

$A_1$ corresponds to the maximum amplitude of said measurement signal; and $t_1$ and $t_2$ correspond respectively to the instants marking the start and the end of said integration time interval F.

Advantageously, the value of this indicator is correlated with the pull-out force so that its value thus calculated can provide a measure of the pull-out force of the implant and therefore of the mechanical stability of the implant.

According to a second alternative form of embodiment, an indicator $I_2$ representative of the degree of insertion of the implant into the receiving bone may also be determined by the processing means as being the impact duration measured from the temporal variation of the impaction force applied for each impact. Specifically, an increase in the area of contact between the implant and the bone during insertion of the implant into the bone leads to an increase in the firmness of the contact between the implant and the bone, which manifests itself in a reduction of the duration of the impact during successive impacts. Put differently, the impact duration, for which the load is transmitted from the percussion tool to the placement ancillary, is indicative of the firmness of the contact between bone and implant and therefore of the degree of insertion of the implant into the receiving bone, on which the primary stability of the implant is dependent.

So, this alternative form of embodiment of calculating the indicator $I_2$ relies on the observation whereby the impact duration, upon each impact, is able to constitute relevant information that allows the mechanical properties of the bone-implant interface and, thereby, the firmness of the bone-implant contact to be characterized accurately and reliably.

Figure 4:
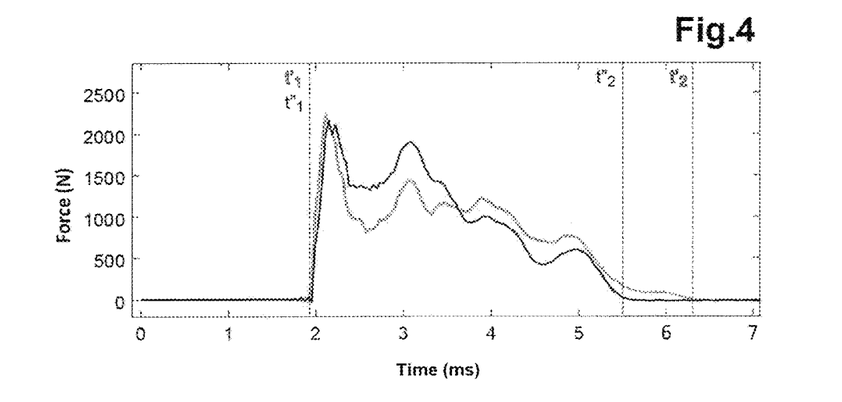
FIG. 4 is a diagram illustrating an example of two measurement signals corresponding to the variation in the force applied to the placement ancillary as a function of time during the various impacts and illustrating the calculation of the indicator representative of the degree of insertion of the implant into the receiving bone according to an alternative form of embodiment.

Thus, according to this alternative form, upon each impact during insertion of the implant (with substantially the same intensity), the force sensor 12 supplies a measurement signal indicative of the temporal variation of the impaction force applied and the duration of each impact is calculated from the temporal variation of the applied impaction force in order to construct an indicator $I_2$ representative of the degree of insertion of the implant as explained above. FIG. 4 illustrates two such signals recorded by the force sensor during two different impacts, under the test conditions set out with reference to FIG. 2. The signal in dotted line corresponds to the signal gathered during the third impact and the signal in solid line corresponds to the signal gathered during the sixth impact. According to one embodiment, the instants t'1, t"1 (and the instants t'2, t"2 respectively) corresponding to the start (and respectively to the end) of the impact for each of these signals have been calculated by determining the bottom time limit (and respectively the upper time limit) for each impact in which the amplitude of the applied impaction force is greater than a predefined threshold value, for example 30 N. This then results in the indicator $I_2$ which corresponds to the duration of the time interval bounded by these two, lower and upper, time limits and calculated as follows: $I_2$=t"2−t"1, namely $I_2$=4.5 ms for the signal corresponding to the third impact and $I_2$=t"2−t"1, namely $I_2$=3.5 ms for the signal corresponding to the sixth impact.

Whatever the alternative form of embodiment adopted for constructing the indicator $I_1$ or $I_2$ representative of the degree of insertion of the implant into the receiving bone, the processing means 30 are therefore designed to test the evolution of the indicator as a function of the number of impacts in order, from this evolution, to evaluate the degree of insertion of the implant into the bone and therefore the primary stability of the implant.

Figure 5:
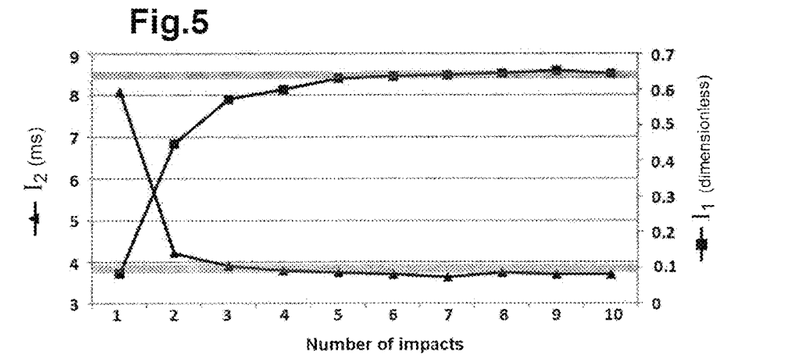
FIG. 5 is a diagram illustrating the variation in the indicator according to one or other of the two alternative forms of embodiment, as a function of the number of impacts.

The signals shown in FIG. 2 correspond to the signals of rank 1, 2, 3, 4, 6 and 10 gathered during the test insertion of the prosthetic acetabulum into a receiving bone under the conditions set out hereinabove with reference to FIG. 2. FIG. 5 represents the corresponding variations in the two indicators $I_1$ and $I_2$ as a function of the number of impacts. It may be noted that the indicator $I_1$ increases over the first six strikes then reaches a steady level from the sixth impact onwards when its value undergoes practically no further change. As far as the indicator $I_2$ corresponding to the impact duration is concerned, it may be noted that after the third impact it continues to vary only very slightly, whereas the overall shape of the signals continues to evolve as far as the sixth impact. After the sixth impact, the signals are more or less superposed, leading to substantially constant values for the two indicators $I_1$ and $I_2$ respectively.

So, in order to determine the degree of insertion of the implant into the receiving bone, the processing means comprise means for testing the convergence of the indicator or $I_2$ toward a steady value as a function of the number of impacts. Thus, the processing means of the invention are, for example, designed to detect when the indicator reaches a saturation level, at which its value undergoes substantially no further change, thereby indicating that the degree of insertion of the implant into the receiving bone is sufficient. Specifically, the fact that the indicator reaches a substantially stable level upwards of a certain number of impacts means that the firmness of the contact between the implant and receiving bone during the insertion process no longer varies, by means of which the degree of insertion is considered to be optimal or, in any event, to be sufficient. The value of the indicator, correlated with the pull-out force, is also taken into consideration by the processing means in order to determine implant stability.

This behavior can be explained by the fact that the implant is driven progressively into the receiving bone during a first phase of the impacts. Thus, the area of bone in contact with the orthopedic instrument increases, leading to an increase in the firmness of the contact resulting in a change in the indicator, particularly by an increase in the indicator in the alternative form in which from the temporal variation in the applied force it measures the mean of the force over a predefined integration time interval, or in a decrease in this indicator in the alternative form whereby the impact duration is measured from the temporal variation in the applied force. After a certain number of impacts (six in the example of FIG. 5), the indicator reaches a steady level because the implant is completely driven into the bone and the area of contact between the bone and the orthopedic instrument can therefore no longer increase, which is why the indicator according to the invention reaches that level. Put differently, the measurement principle of the indicator according to the invention is based on estimating the firmness of the contact between bone and orthopedic instrument, by means of which the degree of insertion of the implant into the receiving bone can be evaluated.

Approaches other than the one that has just been described could also be contemplated for evaluating the degree of insertion from measurement signals recorded by the force sensor. Nevertheless, whatever approach is adopted, the principle underlying the invention, on which the processing of the measurement signals acquired by the force sensor for evaluating the degree of insertion relies, consists in using the variation in the applied impaction force as a function of time for each strike or alternatively, in using the fourier transform of the variation in impaction force as a function of time (in the frequency domain).

According to the foregoing, the degree of insertion of the implant into the receiving bone is thus considered to be sufficient as soon as the processing means 30 detect that the indicator $I_1$ or $I_2$ has reached a stable saturation level signifying that the firmness of the contact between bone and implant is no longer varying.

As an alternative, the degree of insertion of the implant may also be considered to be sufficient when the processing means 30 detect that the indicator has reached a predetermined threshold value, using charts.

The processing means may further be coupled to audible and/or visual alarm means 33 capable of supplying a visible and/or audible indication to the surgeon when the primary stability evaluated by the processing means is deemed to be sufficient, or, put differently, when the indicator reaches a steady level. The surgeon therefore has available in real time reliable information indicating to him that he has reached a sufficient degree of insertion of the implant into the receiving bone and that he no longer needs to continue to impact the implant, thus avoiding any risk of his causing the receiving bone to fracture.

One application of the device and of the method which have just been described is in the placement of hip prosthesis implants, particularly the example of the placement of the prosthetic acetabulum. Of course, still in the context of the placement of total hip prostheses, the invention could also apply to the placement of the femoral stem. Furthermore, other applications of the present invention in the context of orthopedic surgery are also conceivable, covering the placement of implants for knee, shoulder or ankle prostheses and, in general, the placement of any type of orthopedic instrument that needs to be inserted into a receiving bone by impaction.

The invention claimed is:

1. A device assisting with placement of an orthopedic instrument intended to be inserted in a receiving bone by impaction, said device comprising:
    an impactor comprising at least one striking surface designed to impact an impact surface, coupled to an orthopedic instrument, to apply a first impaction force to said orthopedic instrument;
    a force sensor that:
        measures, upon a first impact, said first impaction force applied by the impactor to said impact surface,
        supplies a first measurement signal, the first measurement signal comprising a first temporal variation of said first impaction force, the first temporal variation of the first impaction force being a first signal representative of the first impaction force over a first time duration, the first signal comprising a first plurality of points, wherein each point out of the first plurality of points along the first signal comprises a first amplitude value representative of the first impaction force and a first time value representative of an instant in the first time duration of the first measurement signal; and
    a processor coupled to a memory, wherein the processor:
        is connected to said force sensor,
        receives the first measurement signal including the first temporal variation of the first impaction force,
        calculates a first indicator representative of a degree of insertion of said orthopedic instrument in the receiving bone based on evaluation of the plurality of points in the first temporal variation after the first measurement signal is received, and
        determines an accuracy of a level of insertion of the orthopedic instrument in the receiving bone based on the first indicator.

2. The device according to claim 1, wherein:
    the first indicator, calculated by the processor, comprises an arithmetic mean of the first amplitude values of the first plurality of points over a first time interval of programmable duration on said first measurement signal, and
    a start of the first time interval is defined with respect to an instant corresponding to a maximum amplitude of the first measurement signal.

3. The device according to claim 2, wherein the start of said first time interval coincides with the maximum amplitude of said first measurement signal.

4. The device according to claim 2, wherein said first time interval has a duration of between 1.2 ms and 2 ms, inclusive.

5. The device according to claim 2, wherein the start of said first time interval is defined with a first predetermined delay with respect to the instant corresponding to the maximum amplitude of said first measurement signal.

6. The device according to claim 5, wherein said first time interval has a first predefined duration of less than or equal to 10 ms.

7. The device according to claim 2, wherein said first indicator is calculated using the following equation:

$$I_1 = \frac{1}{A_1 \cdot (t_2 - t_1)} \int_{t_1}^{t_2} A(t) \cdot dt$$

where: A(t) corresponds to an amplitude of said first measurement signal at a first time instant t;
A1 corresponds to the maximum amplitude of said first measurement signal over the first time interval; and
T1 and t2 correspond respectively to the instant marking the start and an instant marking an end of said first time interval.

8. The device according to claim 1, wherein the processor further:
    tests a convergence of said first indicator toward a steady value as a function of a number of the first impact, and
    determines said degree of insertion of said orthopedic instrument into the receiving bone based on the tested convergence of said first indicator.

9. The device according to claim 1, further comprising a placement ancillary, wherein:
    said orthopedic instrument consists of an orthopedic implant, and
    said impactor impacts said orthopedic implant in collaboration with the placement ancillary consisting of a rigid manipulation handle including a distal part defining a head for holding said implant and with a proximal part defining said impact surface.

10. The device according to claim 1, wherein said orthopedic instrument comprises an orthopedic implant surgical rasp comprising:

a part for holding, and an upper end of said part for holding comprising said impact surface.

11. The device according to claim 1, wherein said force sensor comprises an accelerometer.

12. The device according to claim 1, wherein said force sensor is mounted on said at least one striking surface of said impactor.

13. The device according to claim 1, wherein said force sensor is mounted on said impact surface.

14. The device according to claim 1, wherein said force sensor comprises strain gauges.

15. The device according to claim 11, wherein the surgical rasp comprises a femoral rasp for a hip prosthesis.

16. The device according to claim 1, wherein the force sensor further:

measures, after supplying the first measurement signal and upon a second impact, a second impaction force applied by the impactor to the impact surface, and supplies a second measurement signal, the second measurement signal comprising a second temporal variation of the second impaction force, the second temporal variation of the second impaction force being a signal representative of the second impaction force over a second time duration, the second signal comprising a second plurality of points, wherein each point out of the second plurality of points along the second signal comprises a second amplitude value representative of the second impaction force and a second time value representative of an instant in the second time duration of the measurement signal; and wherein the processor further:

stores the first indicator into the memory, receives the second measurement signal, calculates a second indicator based on the second plurality of points after the second measurement signal is received, stores the second indicator into the memory, performs a comparison between the second indicator and the first indicator, and determines an accuracy of a level of insertion of the orthopedic instrument in the receiving bone based on the comparison.

* * * * *